(12) United States Patent
Beck

(10) Patent No.: US 8,444,586 B2
(45) Date of Patent: May 21, 2013

(54) DEGASSING DEVICE

(75) Inventor: Christof Beck, Blitz (DE)

(73) Assignee: Gambro Lundia AB, Lund (SE)

( * ) Notice: Subject to any disclaimer, the term of this patent is extended or adjusted under 35 U.S.C. 154(b) by 293 days.

(21) Appl. No.: 12/937,901

(22) PCT Filed: Apr. 28, 2009

(86) PCT No.: PCT/EP2009/003068
§ 371 (c)(1),
(2), (4) Date: Dec. 17, 2010

(87) PCT Pub. No.: WO2009/132816
PCT Pub. Date: Nov. 5, 2009

(65) Prior Publication Data
US 2011/0092875 A1  Apr. 21, 2011

(30) Foreign Application Priority Data

Apr. 30, 2008 (EP) ..................... 08008247

(51) Int. Cl.
| | |
|---|---|
| A61M 1/00 | (2006.01) |
| A61M 1/14 | (2006.01) |
| A61M 1/36 | (2006.01) |
| A61M 1/38 | (2006.01) |
| A61M 37/00 | (2006.01) |
| B01D 19/00 | (2006.01) |
| B04C 1/00 | (2006.01) |

(52) U.S. Cl.
USPC ....... 604/6.09; 604/4.01; 604/5.01; 604/6.11; 422/44; 422/48

(58) Field of Classification Search
USPC .............. 604/6.09, 4.01, 5.01, 6.11, 6.14, 604/6.15; 422/44, 45, 47, 48
See application file for complete search history.

(56) References Cited

U.S. PATENT DOCUMENTS

| | | | | |
|---|---|---|---|---|
| 3,751,879 | A | * | 8/1973 | Allington ........................ 96/5 |
| 4,009,715 | A | * | 3/1977 | Forberg et al. ................ 604/126 |
| 4,390,351 | A | * | 6/1983 | Matsui et al. ................... 96/209 |
| 4,411,792 | A | * | 10/1983 | Babb ............................. 210/651 |
| 4,690,762 | A | * | 9/1987 | Katsura ........................... 96/212 |

(Continued)

FOREIGN PATENT DOCUMENTS
| | | |
|---|---|---|
| WO | WO 97/40870 | 11/1997 |
| WO | WO 2005/044340 | 5/2005 |

OTHER PUBLICATIONS

PCT International Search Report for PCT/EP2009/003068 completed by the EP Searching Authority on Jun. 26, 2009.

*Primary Examiner* — Adam Marcetich
(74) *Attorney, Agent, or Firm* — Barnes & Thornburg LLP

(57) ABSTRACT

A device for degassing gas bubbles out of a liquid comprises a housing having a liquid inlet, a liquid outlet and a gas bubble outlet. The housing includes a spiral wall defining a spiral flow path for the liquid and a hydrophobic membrane above the spiral wall and between the spiral wall and the gas bubble outlet. The spiral wall forces inward liquid entering the housing through the inlet into a spiral flow along the spiral flow path, and causes an upward flow of the gas bubbles toward the hydrophobic membrane. A method for degassing gas bubbles out of a liquid, e.g., blood, e.g., during hemodialysis, hemofiltration and hemodiafiltration, and use of such a degassing device in an extracorporeal circuit for degassing gas bubbles out of liquid, e.g., blood, e.g., during hemodialysis, hemofiltration and hemodiafiltration, are disclosed.

22 Claims, 8 Drawing Sheets

U.S. PATENT DOCUMENTS

| | | | |
|---|---|---|---|
| 4,919,802 A * | 4/1990 | Katsura | 422/44 |
| 5,541,167 A | 7/1996 | Hsu et al. | |
| 5,618,425 A * | 4/1997 | Mitamura et al. | 210/493.5 |
| 5,632,894 A * | 5/1997 | White et al. | 210/436 |
| 5,651,765 A | 7/1997 | Haworth et al. | |
| 5,849,065 A * | 12/1998 | Wojke | 96/211 |
| 6,176,903 B1 * | 1/2001 | Wamsiedler | 96/208 |
| 6,176,904 B1 * | 1/2001 | Gupta | 96/209 |
| 6,398,955 B1 | 6/2002 | Fumiyama et al. | |
| 2002/0051732 A1 * | 5/2002 | Friedman | 422/44 |
| 2005/0192525 A1 * | 9/2005 | Wieting et al. | 604/6.09 |
| 2007/0118064 A1 * | 5/2007 | Ueda et al. | 604/6.09 |
| 2007/0269340 A1 * | 11/2007 | Dannenmaier et al. | 422/45 |
| 2008/0214978 A1 * | 9/2008 | Sparks et al. | 604/5.01 |

* cited by examiner

DEGASSING DEVICE

CROSS-REFERENCE TO RELATED APPLICATIONS

This application is the U.S. national phase of PCT/EP2009/003068 filed Apr. 28, 2009. PCT/EP2009/003068 claims priority to European patent application EP 08008247.2 filed Apr. 30, 2008. The disclosure of both of EP 08008247.2 and PCT/EP2009/003068 are hereby incorporated herein by reference.

TECHNICAL FIELD

The present disclosure relates to a degassing device, and particularly to a degassing device for liquids, especially for blood, which is used in extracorporeal circuits for the treatment of blood.

DESCRIPTION OF THE RELATED ART

Degassing devices are used in various treatments of blood, such as blood autotransfusion and cell separation during an operation, such as, for example, cardiopulmonary bypass procedures, but also especially in hemodialysis, hemofiltration, haemodiafiltration or plasmapheresis applications. In all these treatments, blood is withdrawn from a patient, flown through a filter, such as a dialyzer, and returned to the patient. As blood is returned to the patient, it is treated for the removal of particles and especially for the removal of bubbles of gas.

Even if these bubbles of gas are only of very small size, they can cause serious damage to body functions by causing air embolism. Air embolism occurs when bubbles of air become trapped in the circulating blood. An embolus in an artery is travelling in a system of tubes which are getting gradually smaller. Eventually, it will block a small artery, which is serious because the blockage will cut off the blood supply to some area of the body. However, the embolus' effect will depend on the part of the body to which the artery supplies blood. If, for example, the embolism prevents blood supply to the brain, tissues will be starved of oxygen, causing them to die, thus likely resulting in permanent brain damage. If the embolus is in a vein, the tube system widens along the direction of the blood flow so that a small embolus may not do much harm until it passes through the heart, after which it enters an artery.

A machine for hemodialysis, hemofiltration, haemodiafiltration or plasmapheresis applications comprises a peristaltic pump for withdrawing blood from a patient through a so-called "arterial line" connected at one end to the vascular circuit of the patient and at the other end to the inlet of the first compartment of a filter, for pumping blood into the filter, and for returning blood to the patient through a so-called "venous line" connected at one end to the outlet of the first compartment of the filter and at the other end to the vascular circuit of the patient. The treatment machine also usually comprises a first blood pressure sensor for measuring the pressure of blood in the arterial line upstream of the pump, a second blood pressure sensor for measuring the pressure of blood in the arterial line downstream of the pump, a third pressure sensor for measuring the pressure of blood in the venous line, a bubble detector for detecting air bubbles in the venous line and a clamp for closing the venous line, for example when air bubbles are detected by the bubble detector.

An arterial line typically comprises the following components connected together by segments of flexible tubes: a first Luer connector for connection to an arterial canula, an arterial bubble trap, a pump hose for cooperating with the rotor of the peristaltic pump of the treatment machine, and a second Luer connector for connection to the inlet of the first compartment of the filter.

A venous line typically comprises the following components connected together by segments of flexible tubes: a first Luer connector for connection to the outlet of the first compartment of the filter, a venous bubble trap, and a second Luer connector for connection to a venous canula. Usually, the first and third pressure sensors of the machine are connected to the arterial and venous bubble trap respectively, when the treatment machine, the arterial line, the venous line and the filter are assembled in view of a treatment.

In the prior art, devices for separating air bubbles out of medical fluids such as blood have been described. They can often also be used for separating out gases other than air. For that reason, air separators of this kind are also described as degassing devices.

Blood degassing devices must be able to reliably and efficiently separate air bubbles from the blood, and further have to be constructed with respect to the mechanical properties and the flow paths being formed that any damage to the blood components is ruled out. It is further desirable for a low level of blood damage to have smooth surfaces on the material side and a structure of the flow paths which is favourable to the flow, with the result that the adhesion of blood corpuscles to surfaces of the air separator and thus a conglomeration of blood corpuscles is avoided. Also, the residence times of the blood in the air separator should be as short as possible, but without deteriorating the air separation as such. It is further desirable to minimize the fill volume of the degassing device.

A conventional degassing device is basically an elongated container which, when in use, is held vertically. The container has an inlet and an outlet for blood which are arranged not to be adjacent. It generally also comprises, in an upper location, a pressure measuring port for connection to a pressure sensor, an infusion port for infusing a liquid (e.g. a drug or a sterile saline solution) and an injection port for adding or removing air into or from the degassing device so as to adjust the level of blood therein.

In use, such degassing devices contain a volume of blood in a lower part which transiently stagnates therein so as to let gas bubbles and micro bubbles escape by gravity and migrate to an upper part of the container full of air, with the result that a conventional bubble trap therefore always comprises a blood/air interface.

GB 2 063 108 A discloses a degassing device having a vertically arranged chamber with a cylindrical section comprising an end fitting having a conical taper with a venting duct at its top. The fluid to be degassed enters beneath the conical section into the chamber. The inlet connection is disposed in such a manner that the fluid flows tangentially into the chamber in the outer peripheral area. Because the fluid is introduced tangentially, it initially flows in a circular flow path, but with the entire fluid motion through the chamber being superimposed upon it, the fluid flows through the chamber in a helical flow path and emerges again at the bottom end of the chamber out of the tangentially arranged outlet connection. The circular motional components of the fluid flow produce centrifugal forces which build up pressure differences in the fluid so that the air bubbles are forced to the middle of the chamber and rise upwards. The separated air bubbles can then be drawn off through the venting bore at the top end of the chamber.

U.S. Pat. No. 6,053,967 discloses an air separator for liquid containing gas bubbles having an essentially cylinder-shaped chamber through which liquid, such as blood, flows essentially in helical flow paths, with the result that air bubbles are driven in a radial direction relative to the longitudinal axis of the chamber because of pressure differences produced by centrifugal forces. The inlet and outlet of the chamber of the air separator are coaxial relative to each other in the longitudinal axis of the chamber. The known air separator also includes a flow-deflection component which includes a rotation-symmetrical base body element whose outer surface faces inflowing liquid as a first deflection surface, which is geometrically defined by rotation of a curve section about the longitudinal axis of the chamber. The first deflection surface has deflection surface deflector vanes, which are curved in planes perpendicular relative to the longitudinal axis of the chamber, with the result that axially inflowing liquid is deflected so that desired helical flow development is induced.

U.S. Pat. No. 5,849,065 discloses a device for separating gas bubbles out of medical fluids, in particular blood, having a substantially cylindrical chamber, an inlet connection arranged in the longitudinal direction of the chamber, an outlet connection and a flow-guide member attached to the inlet connection and having a plurality of flow channels, which extend in a space curve out of the longitudinal direction of the chamber in a direction running substantially tangential to the inner wall of the chamber. An orifice, which is sealed by a hydrophobic membrane, is provided in the cover part of the chamber. Since the outlet orifices of the flow channels are arranged directly underneath the cover part, the membrane is circumflowed by the inflowing fluid, avoiding the formation of dead zones. The device makes it possible to separate out air bubbles with a substantial degree of reliability, without the danger of the hydrophobic membrane becoming obstructed from contact with the blood.

WO 2005/053772 A1 discloses a degassing device comprising a first chamber having an inlet for a liquid and a second chamber having an opening closed by a hydrophobic membrane and an outlet for discharging the liquid, wherein the first chamber has a downstream portion which partially extends within the second chamber and communicates therewith by a passageway. The second chamber has a downstream portion which extends below the passageway and asymmetrically surrounds the downstream portion of the first chamber.

WO 2005/044340 A1 and WO 2005/044341 A1 both disclose an integrated blood treatment module comprising a degassing device which is connected to the second end-cap of the module. The degassing device comprises a first chamber having a lower inlet for a liquid and a second chamber having an upper opening closed by a hydrophobic membrane and an outlet for discharging the liquid. The connecting structure has at least a first and a second conduits defined therein, wherein the first conduit comprises a first end for connection to a discharge tube from the treatment device and a second end connected to the inlet of the first chamber of the degassing device, and the second conduit comprises a first end connected to the outlet of the second chamber of the degassing device and a second end for connection to a blood return tube to a patient.

The blood conditioning device discloses in U.S. Pat. No. 7,108,785 B1 comprises a helical blood acceleration section which includes a helical flow path for impressing centrifugal forces on the entrained bubbles in the blood to concentrate them towards the centre of the flow path, a bubble pick off tube aligned with the centreline of the acceleration section which collects and recirculates the bubbles to the cardiotomy reservoir upstream of the device during operation, and a blood filtration section to intercept the flow of particles in the blood.

U.S. Pat. No. 6,398,955 B1 discloses a blood filter including a housing with a spiral chamber defined between an inner wall and an outer wall of the housing and a centre chamber defined within the inner wall. The spiral chamber extends in a helix shape to surround the centre chamber. The centre chamber has the air bubble outlet. The spiral passage of the spiral chamber surrounds the centre chamber in the range of 180 degrees to 400 degrees. The degassing device further comprises a filter element which divides the inner space into a space which is in communication with the blood inlet and a second space which is in communication with the blood outlet.

SUMMARY

The present disclosure provides a degassing device for separating gas bubbles out of fluids, in particular out of blood.

The proposed degassing device comprises a housing having a liquid inlet, a liquid outlet and a gas bubble outlet, the housing further comprising a spiral wall defining a spiral flow path for the liquid and a hydrophobic membrane placed above the spiral wall and between the spiral wall and the gas bubble outlet, the spiral wall forcing inward flux liquid entering into the housing through the inlet into a spiral flow along the spiral flow path, and causing an upward flow of the gas bubbles towards the hydrophobic membrane.

The degassing device significantly reduces the total volume within the chamber in comparison to the degassing devices known in the art, where air cushions are formed in an upper area. In the present device, no air cushion will form as the bubbles, which are separated from the fluid, are immediately removed from the system through the hydrophobic membrane. In devices in which an air cushion is formed, the inflow must be placed as far away from this upper area in order to stabilize the fluid layer and to avoid renewed introduction of air. This necessitates chambers with a substantial overall height and, as a consequence, the degassing devices will accommodate a relatively large amount of blood. The degassing device according to the present disclosure does not need such height of the chamber, which can in contrast be minimized, thus significantly reducing the blood volume in the degassing device and making the degassing device economic from a material consumption point of view. Such reduced blood volume also minimizes the contact to extracorporeal surfaces, thus reducing the risk of activation of blood components.

As no air cushion or dead zone forms in which air bubbles might accumulate, the degassing device according to the present disclosure avoids the prolonged contact between blood and air and thus reduces the risk of blood clotting. The hydrophobic membrane in the cover part of the degassing device is in direct and complete contact with the fluid.

The blood level in the degassing device is automatically adjusted and limited by the surface of the degassing hydrophobic membrane. As a consequence, no level adjustments are needed during priming as well as during treatment.

The degassing device according to the present disclosure maximizes the advantages which can be gained from the use of a helical or spiral flow within such degassing chamber by means of an extended spiral inside the housing which forces the blood flow into a guided spiral flow.

The proposed degassing device can be used in a system for removing air from a liquid over extended periods of time, without any significant decrease in its effectiveness. This is partly attributable to the fact that the venting membrane is in constant contact with the liquid. In devices wherein the membrane is not permanently contacting the liquid, especially blood, the membrane tends to loose its permeability over time. As the chamber of the degassing device according to the present disclosure is filled with liquid, thus enabling a constant contact of the liquid with the membrane, the degassing device of the present disclosure has a longer life span and requires less monitoring or surveillance by the service personnel. This effect can be even improved by using a specific hydrophobic membrane as described below which can optionally be used as a venting membrane in the degassing device according to the present disclosure.

In the proposed degassing device the blood enters the degassing device tangentially through an inlet which is located at the bottom of the chamber. The flow is forced by a spiral shaped wall inside the degassing device into a spiral flow as shown in FIG. 1. On the way through the degassing device the air bubbles inside the blood stream have time to rise upwards. To guarantee this upwards movement of the air bubbles, the degassing device is to be placed essentially horizontally, i.e. the spiral wall should be placed essentially vertically. The degassing device is covered by a hydrophobic membrane placed on top of the spiral shaped wall without actually touching the wall of the spiral. Because of the spiral flow gas bubbles cannot stick to the membrane to create gas-bubble-foam underneath the membrane.

According to one aspect, a spacing is provided between the hydrophobic membrane and the upper edge of the spiral wall, allowing the blood to be in full contact with the membrane. Upon introduction into the degassing device through the inlet, the fluid containing air bubbles flows into the spiral. While the fluid, e.g. blood, flows through the spiral chamber, the air bubbles move to the vicinity of the inner top surface of the spiral due to the centrifugal force and buoyancy of the air. As soon as the air bubbles touch the hydrophobic membrane, the air will leave the degassing device through the membrane. The air free blood can leave the degassing device through a hole located in the bottom side of the chamber. Thus, the air bubbles are effectively separated from the blood and will immediately leave the system. The separation is performed with virtually the same effectiveness whether the amount of air bubbles is large or small.

The housing may comprise a cylindrical housing having an inlet and an outlet. In one embodiment, the diameter of the cylinder may be larger than its height. A possible ratio between diameter and height may be from about 2.5:1 to 1:1, or between about 2:1 and 1.75:1, or between about 1.9:1 and 1.8:1.

The outlet may be variously configured. For example, the outlet may comprise a nipple which defines the outlet passage and may be moulded integrally with the body of the chamber. The outlet may project axially down in the centre of the bottom wall of the chamber and is configured to receive the end of a tube. The tube may be made an integral part of the outlet. In this case, the tube may additionally be furnished, at the opposite end which is not connected to the housing, with an integrated male luer.

The inlet may also be variously configured. It is, however, important that the inlet is as close as possible to the bottom wall of the chamber in order to reduce the velocity of the flow beneath the membrane. The inlet may comprise a nipple which defines the inlet passage. In one embodiment, the inlet passage may be horizontal and open through the side wall of the body of the housing in a direction tangential to the side wall. The inlet may be molded integrally with the body of the chamber and configured to receive the end of a tube as shown in FIG. 3. The tube may be made an integral part of the inlet. In this case, the tube may additionally be furnished, at the opposite end which is not connected to the housing, with an integrated male luer.

The spiral may be an integral part of the body of the housing (the chamber). It is not connected to the outer wall of the chamber, but has its starting point close to the inlet, with a distance of that starting point from the outer wall of the chamber of from about 2 to 5 mm, or about 3 mm. The starting point of the spiral may overlap the inlet in order to avoid that the flow coming from the inlet is split at the entrance of the spiral.

In one embodiment, the spiral wall height is in a range between 17 mm+/−3 mm. The spiral can have 1.6+/−0.3 rotations, or, in other words, can surround the chamber in the range of about 550 degrees +/−108 degrees. The spiral height may be the same over its full length, but it can also be possible to introduce an increasing height from the blood inlet to the blood outlet region.

The spiral housing may have an inner diameter of about 25 to 40 mm, or of about 30 to 35 mm, or about 32 mm.

The distance between the top edge of the spiral wall and the hydrophobic membrane can be in the range of 1.5 mm+/−0.5 mm. A larger or smaller distance generally results in a decrease of the degassing efficiency.

The degassing device is especially effective in removing air from a fluid for fluid flow rates of up to 350 ml/min. Flows below 100 ml/min will result in a decrease in efficiency in removing air from the fluid, even though the degassing device can also be used at lower flow rates.

To improve the efficiency with regard to higher flow rates, the housing can be designed for accommodating a larger fluid volume. In this case, the distance of the hydrophobic membrane from the top edge of the spiral wall should remain the same as described before. Further, the spiral should remain the same in terms of rotations within the chamber. Otherwise, the dimensions can be adapted to an increased size of the degassing device.

The distance between the inner wall of the degassing device and the spiral may be equal to the distance of the outer channel which is generated by the spiral as shown in FIG. 2.

The housing can be formed from any material which is a sufficiently rigid, impervious material and which can withstand a sterilization treatment usually applied to devices used for extracorporeal circulation circuits, for example a transparent engineering plastic material such as polyurethane, polycarbonate, polystyrene, polymethylmethacrylate or polypropylene. Additionally, all of the surfaces of the housing which contact the liquid should be readily wettable by the liquid. In a possible embodiment, the housing is made from polyurethane. The polyurethane can be a thermoplastic polyurethane (TPU) or it can be a two-component polyurethane which is produced by reacting aromatic di- or polyisocyanate (e.g., MDI or modified MDI) or aliphatic diisocyanate (e.g., HDI or $H_{12}$-MDI) with polyether or polyester polyol. In one embodiment of the invention, the housing is made from a polyurethane which is obtained by reacting modified MDI (Desmodur® PF, Bayer MaterialScience AG) and a castor-oil based polyol (Polycin®, CasChem, Inc.). In another embodiment, the housing is made from polycarbonate.

The housing or the body of the housing can additionally be coated. In a possible embodiment, the housing or the body of the housing is treated with a polyurethane solution, for example a 40 wt.-% solution of a polyurethane produced from modified MDI (Desmodur® PF, Bayer MaterialScience AG) and a castor-oil based polyol (Polycin®, CasChem, Inc.) in methyl isobutyl ketone (MIBK). The housing or body may be treated with such solution by spraying or dipping, followed by drying. Drying may be performed at room temperature.

The degassing device according to one general implementation comprises a protective member or cover for protecting the hydrophobic membrane against external force and for limiting the deformation of the hydrophobic membrane when the pressure of the liquid within the degassing device exceeds a limit. The cover does not touch the upper side of the hydrophobic membrane, but leaves a spacing between its upper side and the membrane.

The cover has a cylindrical configuration and includes, in one embodiment, a generally flat top wall and a downturned, generally cylindrical side wall. FIG. 4A displays an aerial view of the cover; FIG. 4B displays the interior view including the membrane. FIG. 4C shows the housing including the spiral body and the cover.

The cover and the body of the chamber may be joined in any suitable manner. For example, the lower end of the cover side wall may include an annular channel formed in a flange which is configured in such a manner to receive the open upper end of the body of the chamber. The cover and the body may then be joined at the channel, for example by bonding or welding, so that the entire unit is disposed of when the element needs replacement. The cover may also be removably positioned on the chamber for easy replacement when needed.

The material the cover is made from may be the same as the one used for the body of the chamber. The element can have at least one opening which will allow the air which leaves the chamber through the membrane to pass through the element as shown in FIG. 4. In general, it might be sufficient to have a single opening, such as, for example, in the central part of the cover, which may have a size from about 1 to 3 mm in diameter, even though said diameter is not crucial as long as the air will be able to readily pass through the cover and as long as, at the same time, the cover remains stable enough to fulfill its protective function. However, it is also possible to use a protective element with more openings which may be larger or smaller in diameter. For example, the cover may be constructed to comprise numerous small openings across its surface.

The degassing device according to the present disclosure comprises a hydrophobic membrane which will allow for the air bubbles to directly leave the system. In one embodiment, the membrane may be attached to the underside of the cover by bonding or welding to allow a free flow of gas from the housing. In one embodiment, the membrane may be welded into the cover, and may additionally be fixed at the periphery with a polyurethane cord which is welded onto the weld seam of the membrane.

The membrane may extend over the full diameter of the chamber. However, the membrane may also have a smaller diameter than the housing or cover, respectively, and may, for example, be positioned in the centre of the chamber and cover. In this case, the cover has to be configured in such a manner to allow the adjustment of such a smaller membrane.

Various hydrophobic membranes may be used together with the degassing device of the present disclosure. The hydrophobic membrane can be made from a polypropylene, polyethylene, polyurethane, polymethylpentene or polytetrafluoroethylene. The pore size must be sufficiently small, about 8 µm, e.g. between 0.1 to 8 µm, or between 0.1 to 3 µm to adequately prevent the passage of liquid through the membrane. The membrane may also comprise an additional backing as a support, i.e. it may comprise two different layers. Such hydrophobic membranes may additionally be coated or modified with surfactants, such as, for example, siloxanes of the general type $R_n H_{2-n} SiO$, wherein n is 1 or 2 and R is a hydrocarbon group having 1 to 18 carbon atoms; polysiloxanes with a monomer unit of the type $[-Si(R_1)_2-O-]_n-$, wherein $R_1$ hydrocarbon groups and n is a number representing the number of units in the polymer, such as, for example, polydimethylsiloxane; or quaternary ammonium salt derivatives of silicone compounds. One suitable polysiloxane (because of its ready availability and ease of application) is polydimethylsiloxane. However, other silicone resin prepolymers can be used, including polymethylethylsiloxane, polydiethylsiloxane, polydipropylsiloxane, polydihexylsiloxane, polydiphenylsiloxane, polyphenylmethylsiloxane, polydicyclohexylsiloxane, polydicyclopentyl siloxane, polymethylcyclopentylsiloxane, polymethylcyclohexylsiloxane, polydicycloheptyl siloxane, and polydicyclobutyl siloxane. Cyclic siloxane oligomers like octamethylcyclotetrasiloxane, decamethylcyclopentasiloxane or dodecamethylcyclohexasiloxane are other examples of suitable compounds. The membrane may also be coated with a mixture of a polysiloxane and silicon dioxide. It may also comprise as a coating, alone or together with the coatings mentioned before, biologically active substances such as anticoagulants, for example heparin or hirudin.

In one embodiment, the membrane used is a polytetrafluoroethylene membrane, such as, for example a membrane selected from standard GORE™ Medical Membranes, for example MMT-323 (0.2 µm). The membrane may be coated with a mixture of polydimethylsiloxane and silicon dioxide, such as SIMETHICONE or the compound marketed by Dow Corning Corp. under the trade name ANTIFOAM A®. A process for coating polymer surfaces with ANTIFOAM A® is disclosed in U.S. Pat. No. 5,541,167.

In a possible embodiment of the proposed degassing device, the deaeration membrane comprises a porous polytetrafluoroethylene (PTFE) sheet having a thickness of from 0.15 to 0.30 mm, more preferably from 0.20 to 0.25 mm, coated with a composition comprising >60 wt. % polydimethylsiloxane (CAS:63148-62-9), 7-13 wt. % methylated silica (CAS: 67762-90-7), 3-7 wt. % octamethylcyclotetrasiloxane (CAS:556-67-2), 3-7 wt. % decamethylcyclopentasiloxane (CAS: 5541-02-6), 1-5 wt. % dimethylcyclosiloxanes and 1-5 wt. % dodecamethylcyclohexasiloxane (CAS:540-97-6), which can be purchased from Dow Corning Corp. under the trade name Antifoam A®.

The membrane is coated with a defined amount of a defoaming agent. The amount of the defoaming agent present on one face of the membrane may range from 4.25 µg/mm$^2$ to 10 µg/mm$^2$, or even from 4.25 µg/mm$^2$ to 7.10 µg/mm$^2$. In a possible embodiment, only one face of the membrane is coated.

The membrane may exhibit an even or uniform distribution of silicon dioxide (silica) particles throughout the entire coated surface of the membrane, including the inner, middle and outer regions of the membrane. The number of silica particles may be in the range of from 22000 to 32000 particles per mm$^2$, or even from 25000 to 30000 particles per mm$^2$.

The membrane may have a pore size that is sufficiently small to keep bacteria from passing through the membrane. A desirable mean average pore size is 0.2 µm or smaller.

The membrane can be prepared by coating a porous PTFE membrane with a solution of the defoaming agent by dip-coating the membrane in the solution or spray-coating the solution onto the membrane. For obtaining a uniform coating, it is preferred to spray-coat the solution on the membrane. The person skilled in the art is familiar with methods of spray-coating a solution onto a membrane. In a preferred embodiment, a two-substance nozzle employing air, steam or other inert gases to atomize liquid is used for spray-coating. The pressure of the atomizing gas is preferably greater than 0.3 bar to achieve a large specific surface and uniform distribution. The nozzle orifice preferably ranges from 0.3 to 1 mm. In a preferred embodiment, the nozzle produces a full circular cone with an aperture of from 10° to 40°. The mass flow of the solution, the distance between the nozzle and the membrane to be coated, and the lateral relative velocity of the membrane and the nozzle may be selected to produce a coating comprising from 4.25 µg/mm$^2$ to 10 µg/mm$^2$, or even from 4.25 µg/mm$^2$ to 7.10 µg/mm$^2$ of defoaming agent (after removal of solvent present in the solution). In a possible embodiment, a nozzle is used which sprays the solution with a mass flow of about 5-10 ml/min, or 7.5-9 ml/min, or 8-8.5 ml/min onto the membranes which are transported past the nozzle at a velocity of about 175-225 cm/min, or 190-210 cm/min, or even 200 cm/min.

The defoaming agent may be dissolved in an appropriate solvent before using it for coating a membrane. Such a solution may contain the defoaming agent in a concentration of from 0.1 wt.-% to 20 wt.-%, or from 1 wt.-% to 10 wt.-%, or from 3 wt.-% to 8 wt.-%.

The solvent for the defoaming agent used in the present disclosure is not particularly limited, if the polysiloxane compound, the silicon dioxide particles and the solvent are appropriately mixed, and if no significant difficulties are caused by phase separation. However, it is proper to use aliphatic hydrocarbons such as n-pentane, i-pentane, n-hexane, i-hexane, 2,2,4-trimethylpentane, cyclohexane, methylcyclohexane, etc.; aromatic hydrocarbons such as benzene, toluene, xylene, trimethylbenzene, ethylbenzene, methyl ethyl benzene, etc.; alcohols such as methanol, ethanol, n-propanol, i-propanol, n-butanol, i-butanol, secbutanol, t-butanol, 4-methyl-2-pentanol, cyclohexanol, methylcyclohexanol, glycerol; ketones such as methyl ethyl ketone, methyl isobutyl ketone, diethyl ketone, methyl npropyl ketone, methyl n-butyl ketone, cyclohexanone, methylcyclohexanone, acetylacetone, etc.; ethers such as tetrahydrofuran, 2-methyltetrahydrofuran, ethyl ether, npropyl ether, isopropyl ether, diglyme, dioxane, dimethyldioxane, ethylene glycol monomethyl ether, ethylene glycol dimethyl ether, ethylene glycol diethyl ether, propylene glycol monomethyl ether, propylene glycol dimethyl ether, etc.; esters such as diethyl carbonate, methyl acetate, ethyl acetate, ethyl lactate, ethylene glycol monomethyl ether acetate, propylene glycol monomethyl ether acetate, ethylene glycol diacetate, etc.; and amides such as N-methylpyrrolidone, formamide, N-methyl formamide, N-ethyl formamide, N,N-dimethyl acetamide, N,N-dimethyl acetamide, etc. Particularly preferred are aliphatic hydrocarbons such as n-pentane, i-pentane, n-hexane, i-hexane, 2,2,4-trimethylpentane, cyclohexane, methylcyclohexane, etc. N-hexane is especially preferred as a solvent in the context of the present invention.

In a possible embodiment of the spray-coating process, the solution of the defoaming agent is cooled down before application in order to avoid evaporation of the solvent during the spray-coating process. The solution used in the spray-coating process may be cooled down to a temperature of from 0 to 15° C., or from 0 to 10° C., or from 0 to 5° C.

The coated membrane is then dried, e.g. at room temperature, for about 30 minutes to two hours, e.g. for about one hour. However, it is also possible to dry the membranes at elevated temperatures of up to 200° C. to shorten the time that is needed for drying. In case the amount of coating (in weight per mm$^2$) resulting from the first coating procedure is below the desired range, the coating process described above can be repeated on the same membrane.

Further features and embodiments will become apparent from the description and the accompanying drawings.

It will be understood that the features mentioned above and those described hereinafter can be used not only in the combination specified but also in other combinations or on their own, without departing from the scope of the present disclosure.

Various implementations are schematically illustrated in the drawings by means of an embodiment by way of example and are hereinafter explained in detail with reference to the drawings. It is understood that the description is in no way limiting on the scope of the present disclosure and is merely an illustration of a possible embodiment.

DETAILED DESCRIPTION

Figure 1:
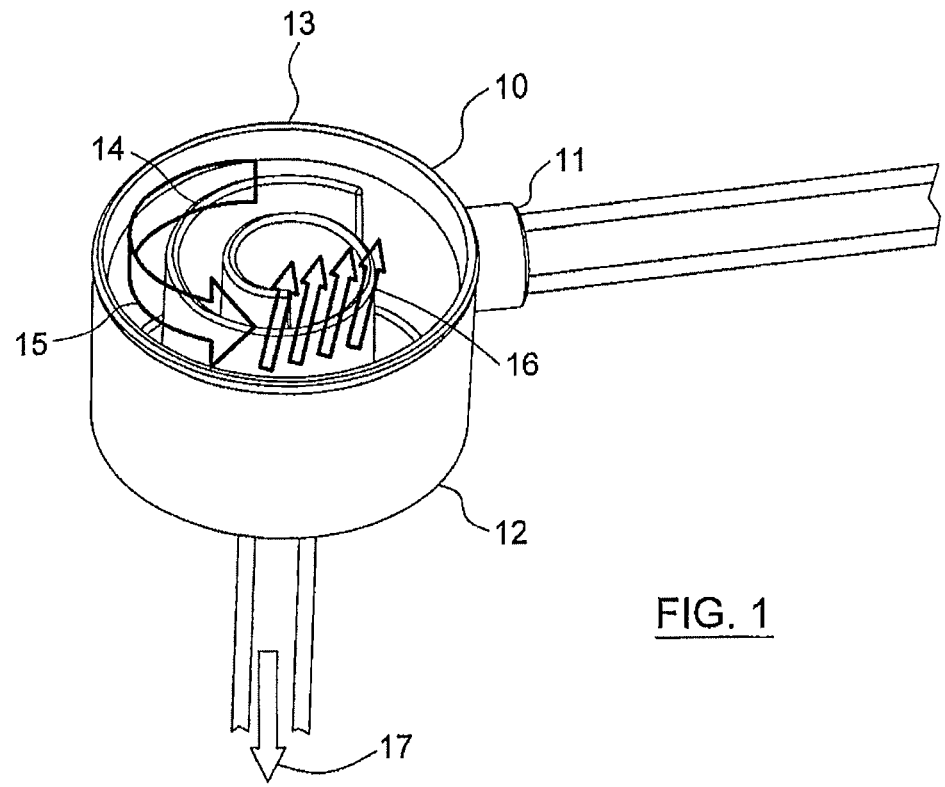
FIG. 1 shows an embodiment of the proposed degassing device.

FIG. 1 shows a possible embodiment of the degassing device as proposed in the present disclosure. As shown in FIG. 1, a liquid, particularly blood enters the degassing device 10 tangentially through an inlet 11 which is located at a bottom 12 of a chamber 13 of the degassing device 10. The flow of the entered liquid is forced by a spiral shaped wall 14 inside the degassing device 10 into a spiral flow as shown by an arrow 15. On the way through the degassing device 10 gas bubbles inside the liquid stream have time to rise upwards as indicated by arrows 16. To guarantee this upwards movement of the gas bubbles, the degassing device 10 has to be placed essentially horizontally, i.e. the spiral wall 14 must be placed essentially vertically. After having passed the chamber 13 in a spiral flow the gas free liquid stream can leave the degassing device 10 through an opening in the bottom 12 of the chamber 13 as shown by arrow 17.

Figure 2:
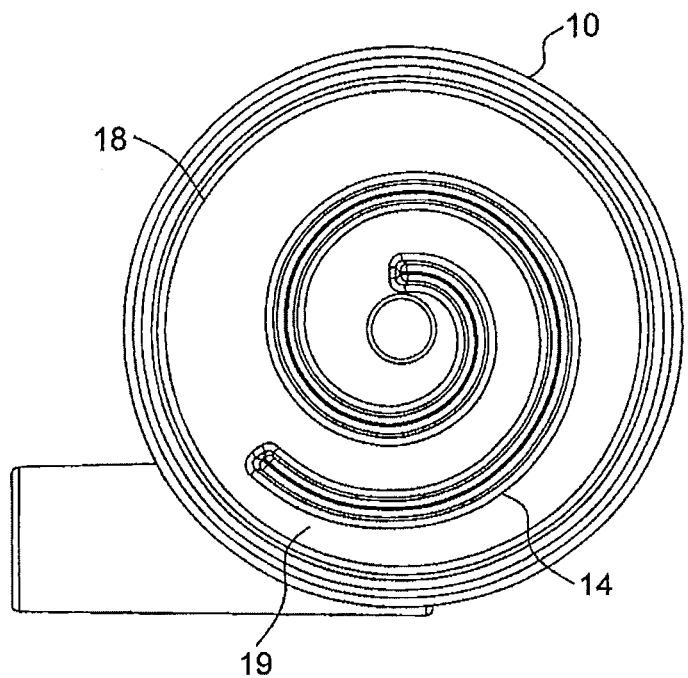
FIG. 2 shows a top view of another embodiment of the proposed degassing device.

FIG. 2 shows a top view of another embodiment of the proposed degassing device. FIG. 2 clearly shows that the distance between an inner wall 18 of the degassing device 10 and a spiral wall 14 inside the degassing device 10 may be equal to the distance of an outer channel 19 which is generated by the spiral wall.

Figure 3:
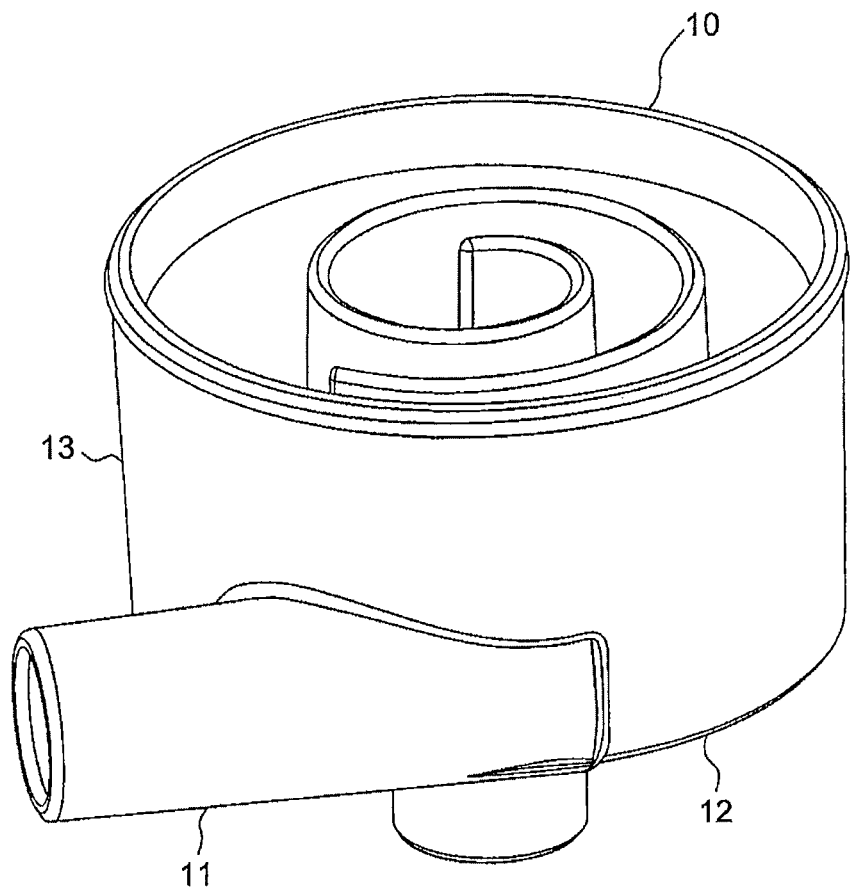
FIG. 3 shows a further embodiment of the proposed degassing device with an integrally molded inlet.

FIG. 3 shows a further possible embodiment of the proposed degassing device with an integrally moulded inlet 11. The inlet 11 of the degassing device 10 may be variously configured. It is, however, important that the inlet 11 is as close as possible to a bottom wall 12 of a chamber 13 of the degassing device 10 in order to reduce the velocity of the flow beneath a hydrophobic membrane which is to be provided according to the present disclosure. As shown in FIG. 3, the inlet passage may be horizontal and open through a side wall of the body of the housing in a direction tangential to the side wall. The inlet 11 may further be moulded integrally with the body of the chamber 13 and configured to receive the end of a tube.

Figure 4A:
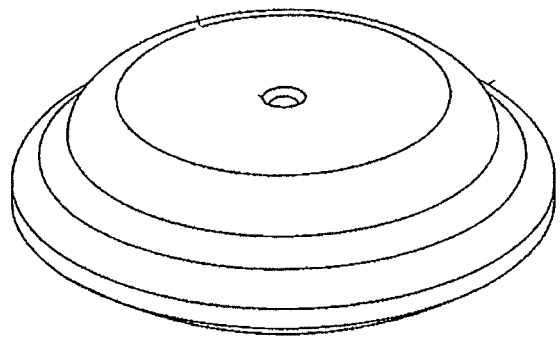
FIG. 4A displays an aerial view of a cover, FIG. 4B displays an interior view including a respective hydrophobic membrane.
Figure 4B:
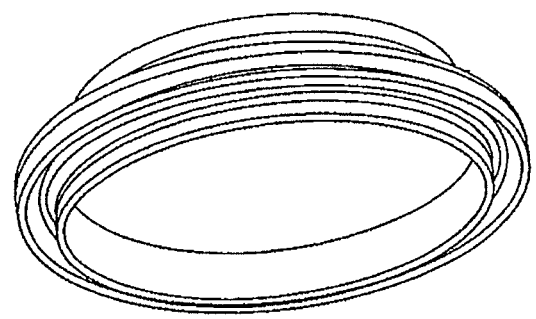
FIG. 4 shows still another embodiment of the proposed degassing device.
FIG. 4C shows a housing including a spiral body and the cover.
Figure 4C:
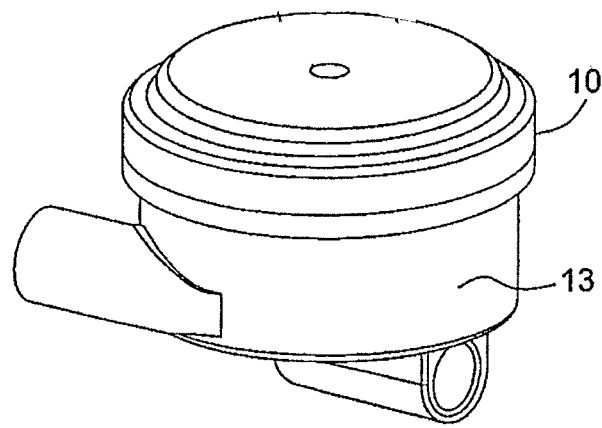

FIG. 4 shows a further embodiment of the proposed degassing device. FIG. 4A displays an aerial view of a cover, the cover having a cylindrical configuration and includes, as shown in FIG. 4A, a generally flat top wall and a down turned, generally cylindrical side wall. FIG. 4B displays an interior view including a hydrophobic membrane. FIG. 4C shows a housing of the proposed degassing device including a spiral body and the cover. The cover can have, as shown in FIG. 4, at least one opening which allows gas which leaves the chamber through the hydrophobic membrane to pass through that opening. In general, it might be sufficient to have a single opening, such as for example in the central part of the cover.

Figure 5:
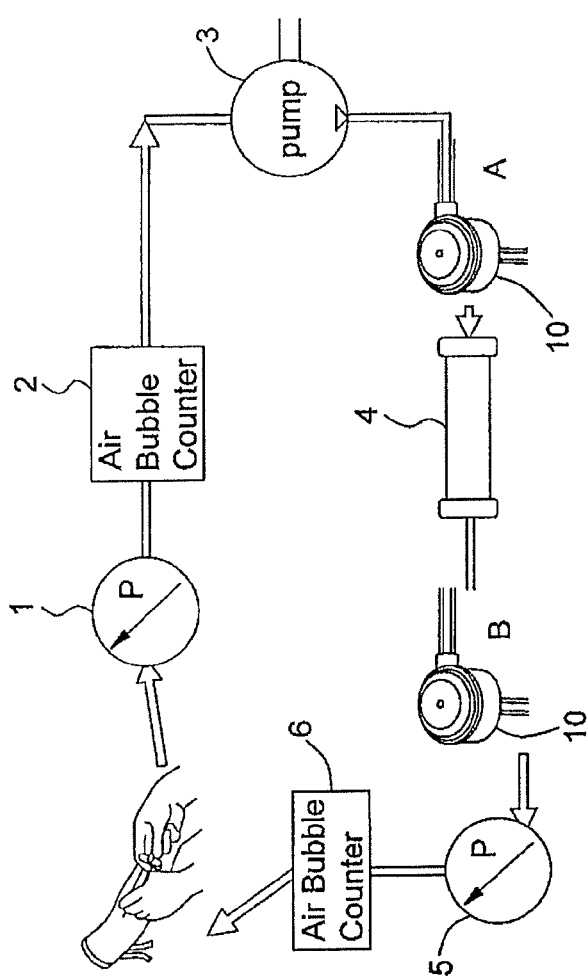
FIG. 5 shows a dialysis setup including an embodiment of the proposed degassing device.

FIG. 5 shows a further possible degassing device which is positioned within a standard dialysis setup on the venous or the arterial side. Such a setup may comprise a pressure sensor 1, a first air bubble counter 2, a pump 3, a degassing device A, a dialyzer 4, optionally a second degassing device B, a second pressure sensor 5 and a second air bubble counter 6.

In one embodiment, the degassing device is positioned on the arterial side of the system, i.e. before the dialyzer in order to effectively remove any air which may be present in the system before such air enters the dialyzer (FIG. 5, degassing device A). In this setup, the pump should be located before the degassing device as any device located before the degassing device may cause an air-in-blood-alarm.

The setup should further comprise an air bubble counter on the arterial side for detecting air in the system. Optionally, a second degassing device may be located on the venous side after the dialyzer as a safety measure (FIG. 5, degassing device B). Such a second degassing device may then remove any remaining air bubbles which have passed or been generated during the passage of the dialyzer.

In another embodiment, the dialysis setup having an arterial degassing device and an optional second venous degassing device comprises an air bubble counter located before the pressure sensor.

In still another embodiment, if a degassing device is mounted in the set which is optimized for a certain flow, such as, for example 350 ml/min or less, it might prove advantageous to reduce the blood flow appropriately. The pump may automatically decrease the blood flow in case of an air-in-blood-alarm to a flow below the optimum of the degassing device.

FIGS. 6 to 11 are described in connection with the following described examples.

EXAMPLES

The spiral degassing device according to the present disclosure shows an exceedingly well performance with regard to degassing of a liquid, especially of blood, both in in vitro and in in vivo tests.

1. Removal of Air In Vitro

Figure 6:
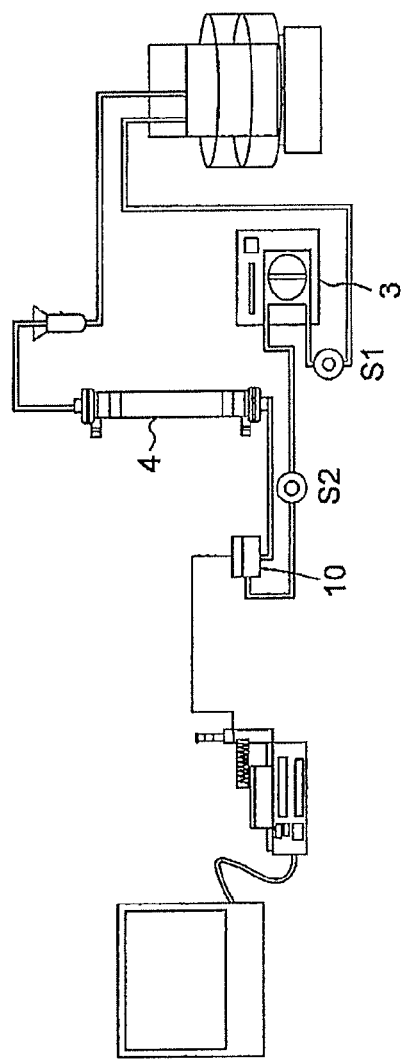
FIG. 6 shows a setup including a possible embodiment of the proposed degassing device for an in vitro test with bovine blood.

In an in vitro test with bovine blood (hematocrit between 32 and 40, total protein content: 60-80 g/l) the efficacy of the degassing device according to the present disclosure was tested by injecting air into the corresponding system (FIG. 6). The setup essentially consisted of a circular flow of blood, comprising one liter of blood (bovine blood) at a temperature of 37° C., a pressure manometer, a degassing device according to the present disclosure, a dialyzer (Polyflux® 170 H, Gambro), a drip chamber and the corresponding tubing. Further, the system comprised a first air injection port S1 and a second air injection port S2, with the first air injection port S1 being located before and the second air injection port S2 being located after the pressure manometer. The amount or volume of air which left the degassing device was determined by measuring the amount of water which was eliminated from a tube containing water and into which the air coming from the degassing device was introduced. The amount of air introduced into the system via the injection ports can of course be varied. The air injection can be done in a continuous fashion or as a bolus. The flow was adjusted to $Q_B$=300 ml/min, the venous pressure was adjusted to 100 mmHg.

The degassing device used had an inner diameter of 32 mm and a spiral height of 17 mm over the total length of the spiral. The spiral had a rotation of 1.6. The distance of the membrane from the upper rim of the spiral was 1.5 mm. The membrane was a MMT-323 (0.2 µm) PTFE membrane from GORE Medical Membranes, coated with a solution comprising 5% Antifoam A® and 95% of hexane as solvent.

Figure 7:
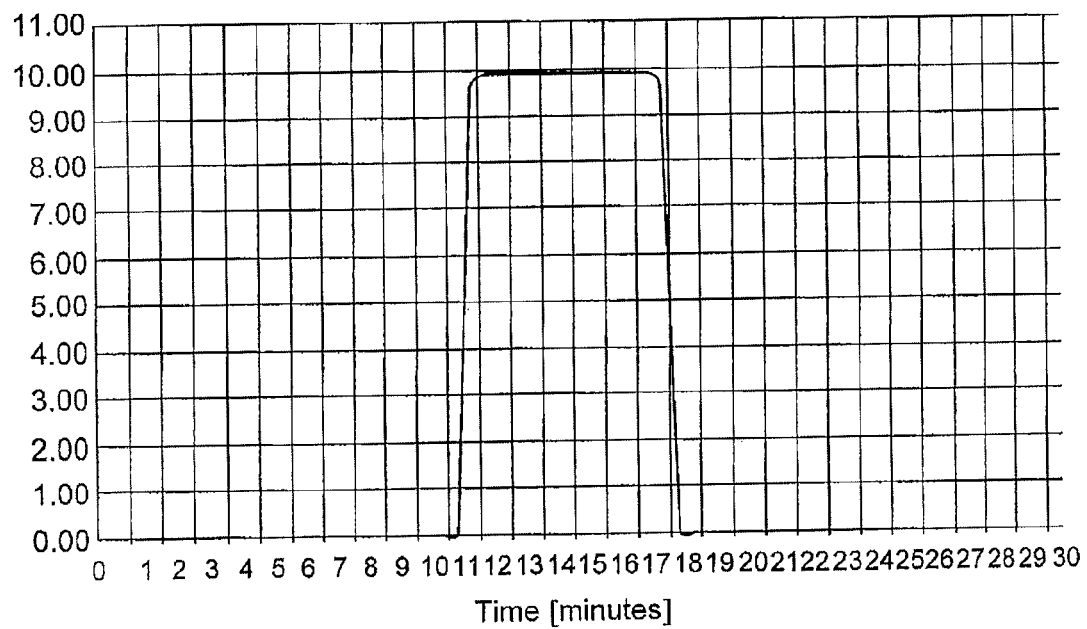
FIG. 7 shows a possible degassing profile of the setup of FIG. 6.

FIG. 7 shows the removal of a bolus of 10 ml, injected at injection port S1, i.e. on the arterial side of the system.

The injected air is completely removed from the system, no air remains in the system or the degassing device either as bubbles in the fluid or as an air cushion. The degassing is achieved within a very short period of time, i.e. within seconds. Controls with saline instead of blood showed that there is virtually no difference between the degassing of the liquids, i.e. blood is degassed as good as the significantly less complex saline liquid.

Figure 8:
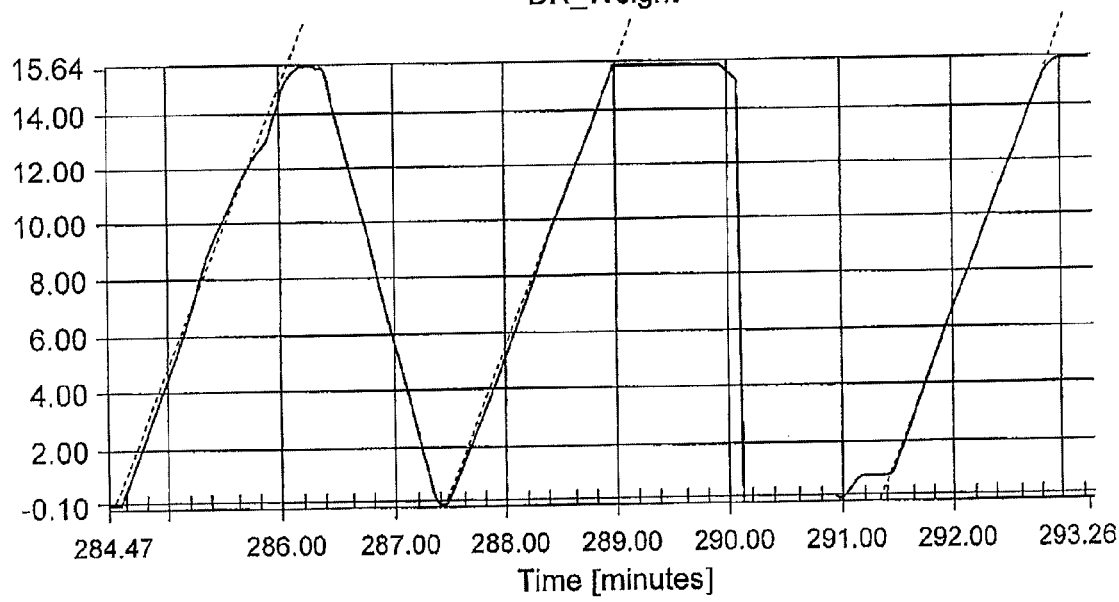
FIG. 8 shows another degassing profile of the setup of FIG. 6.

FIG. 8 shows the removal of a continuous injection of 10 ml/min of air at injection port S1 (arterial side), about 4.5 hours after the test had been started. As can be seen, the air was removed from the system as fast as it was introduced into the system, i.e. with a velocity of 10 ml/min, resulting in a straight slope. This test also shows that the proposed degassing device is able to provide for highly improved degassing efficiency.

Figure 9A:
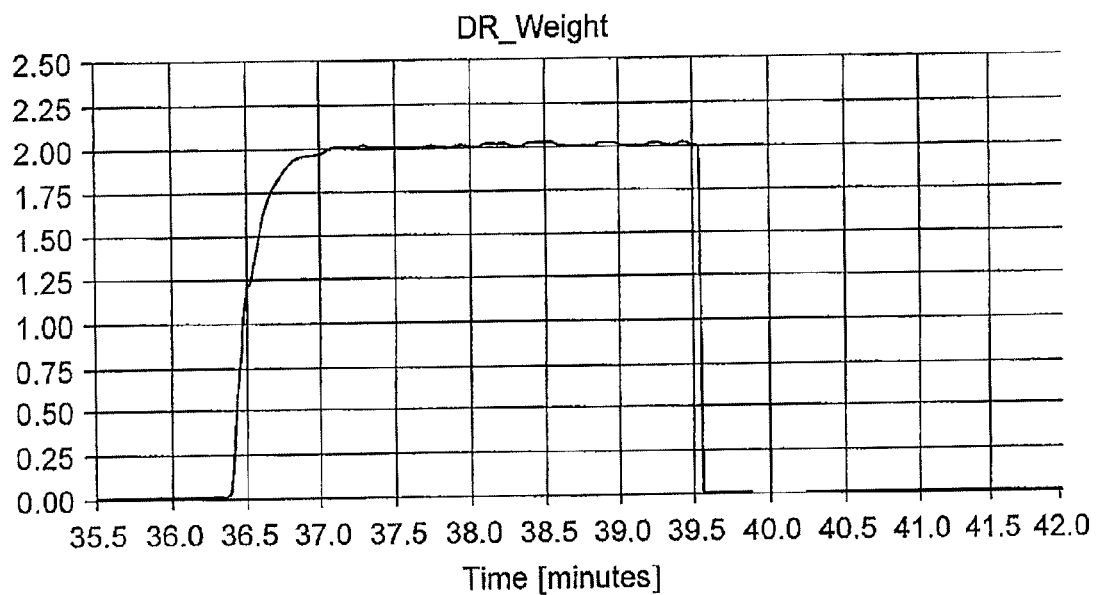
FIG. 9 shows a degassing profile of a standard degassing device (FIG. 9B) in comparison with a degassing profile of an embodiment of the proposed degassing device (FIG. 9A)
Figure 9B:
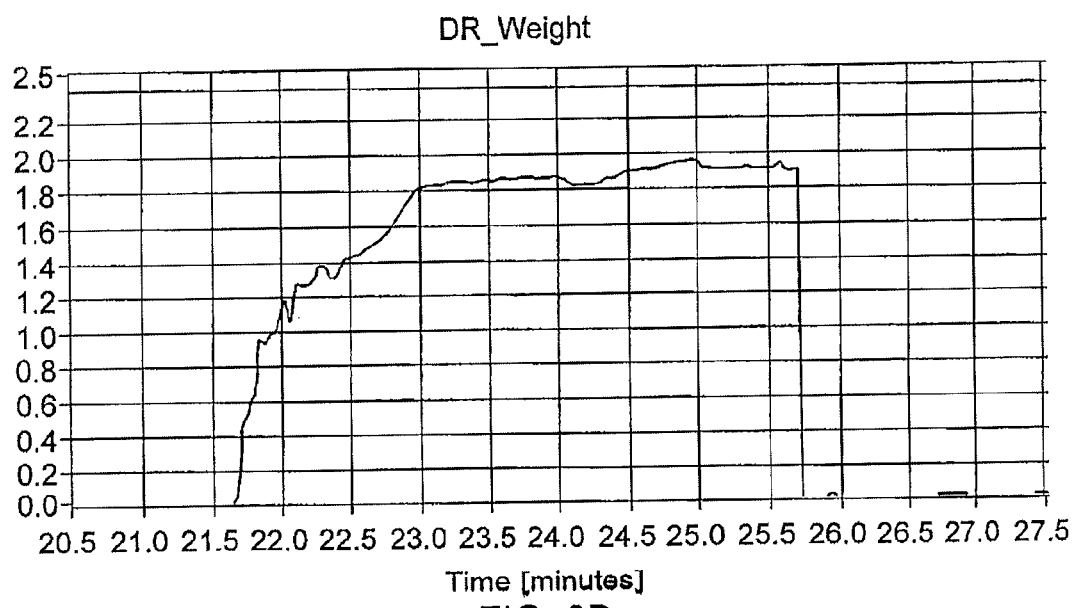

For comparison, FIG. 9B shows the degassing profile of a standard degassing device. A bolus of 2 ml was injected at injection port S1 (arterial side). As can be deduced from the drawing, 1.5 min are needed for removing 1.8 ml of the injected air. The proposed degassing device under the same conditions removes a 2 ml bolus in about 0.5 min (FIG. 9A).

2. Removal of Air In Vivo

Figure 10:
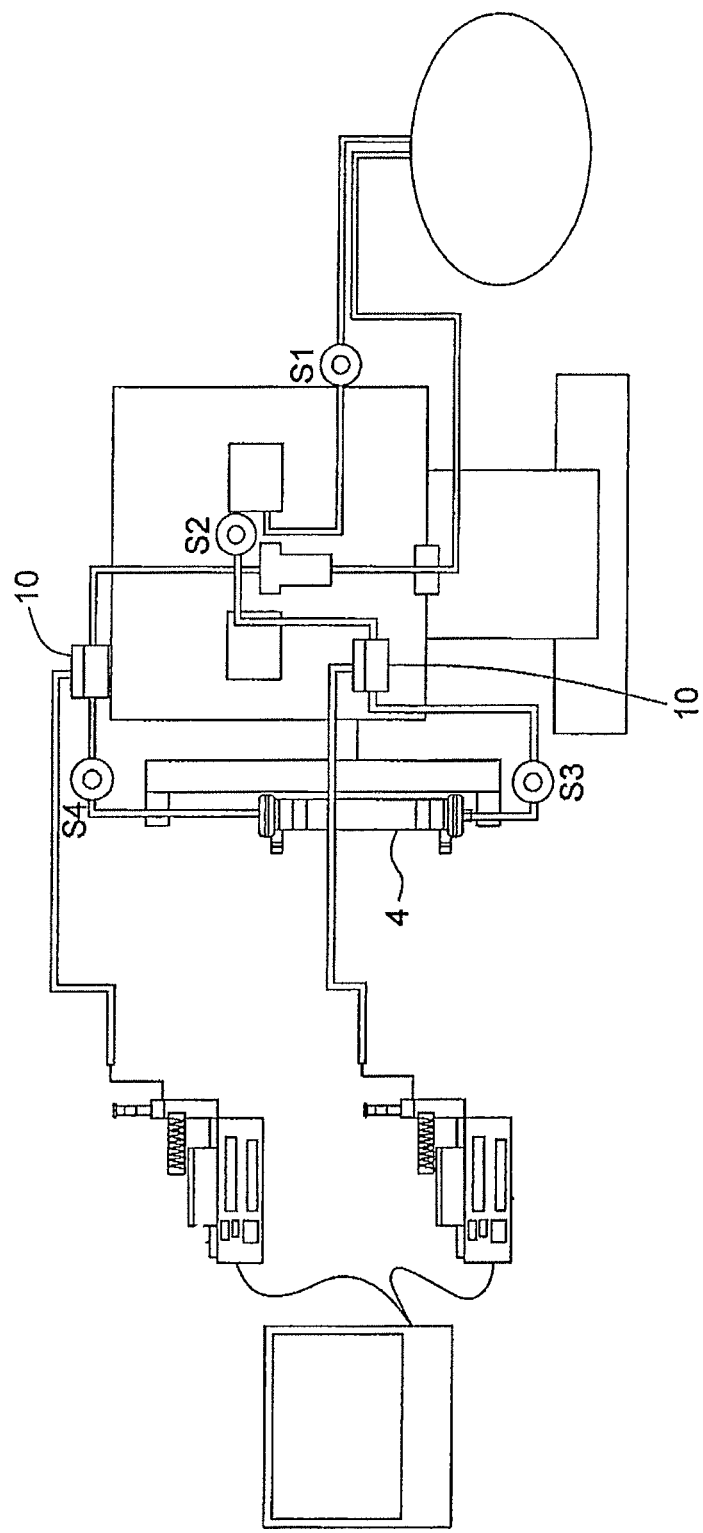
FIG. 10 shows a dialysis setup including a further embodiment of the proposed degassing device, the dialysis setup being used for in vivo tests with sheep.

The same degassing device as described in context of Example 1. above was used also for in vivo tests with sheep, based on a standard dialysis setup including an AK 200 Ultra dialysis machine and a Polyflux® 170 H dialyzer (FIG. 10). The system had again injection ports S1 to S4 as shown in FIG. 10, positioned on the arterial or the venous side of the dialyzer. The system further included two degassing devices according to the present disclosure (see Example 1.) which were positioned before (arterial side) and after (venous side) the dialyzer, respectively.

After the priming of the system the dialysis was performed at a venous pressure of 100 mmHg. The $Q_B$ was 300 ml/min. A first air injection (2 ml bolus) was performed 20 min after the start of the priming, a second air injection (2 ml bolus) was performed 65 min after the start. A third air injection (5 ml bolus) was performed after 125 min, a fourth air injection (continuous boli of 1, 2, 5 and 10 ml/min) after 185 min. A fifth and last bolus of 10 ml air was injected after 205 min.

Figure 11:
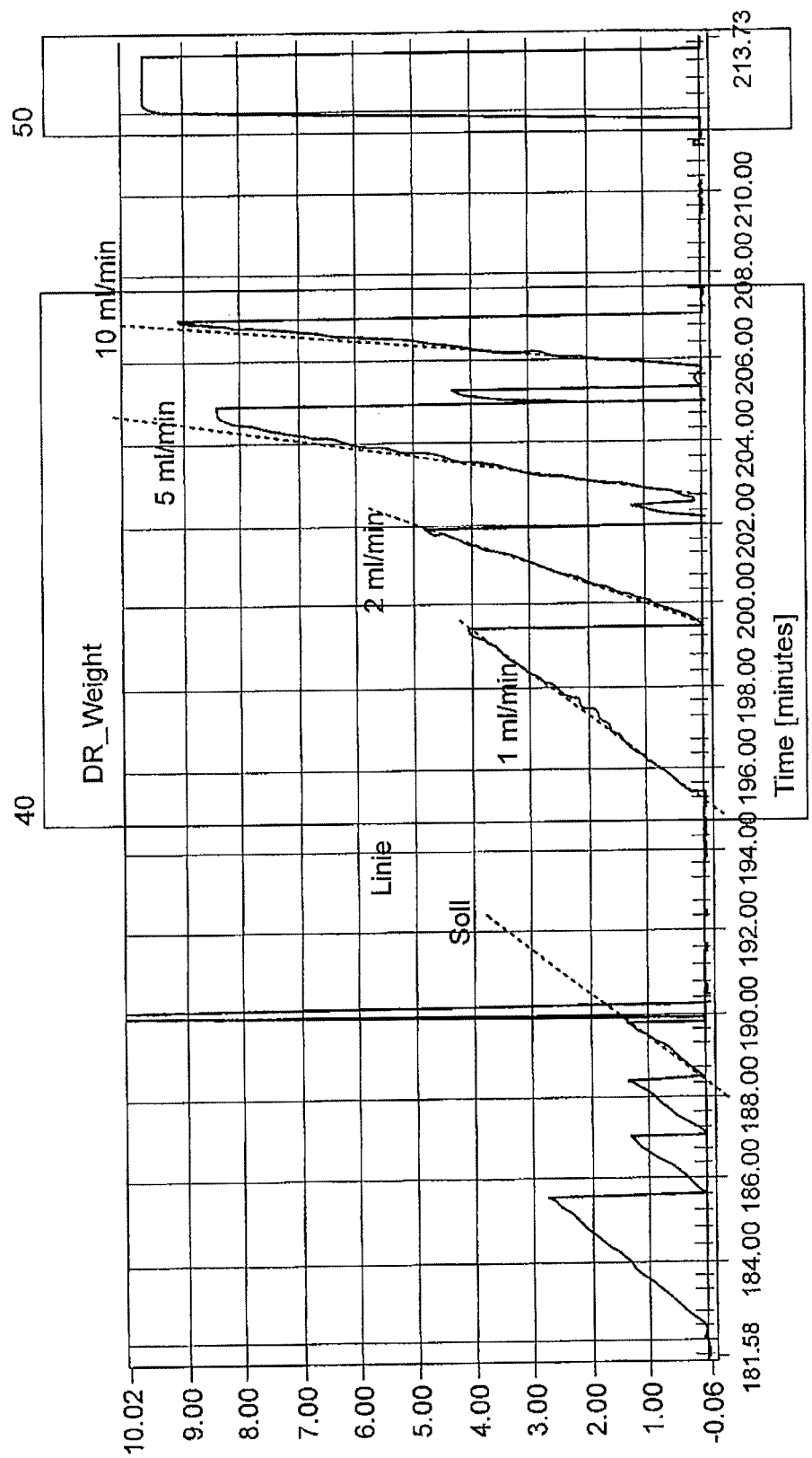
FIG. 11 shows a degassing profile for the dialysis setup of FIG. 10.

FIG. 11 exemplarily shows the profile for the fourth air injection, including four consecutive continuous injections of 1, 2, 5 and 10 ml/min (4), and the profile for the fifth bolus of 10 ml after almost 3.5 hours (5). The profile on the left displays a control injection directly before the degassing device measuring the air which is removed.

| Injection No. | Bolus [ml] | Injection Site | Air detected by ABC [ml] |
|---|---|---|---|
| 1 | 2 | S2 | 0.00 |
| 2 | 2 | S2 | 0.00 |
| 3 | 5 | S1 | 0.02 |
| 4 | 1* | S1 | 0.00 |
| 4 | 2* | S1 | 0.00 |
| 4 | 5* | S1 | 0.00 |
| 4 | 10* | S1 | 0.00 |
| 5 | 10 | S1 | 0.00 |

*continuous injection [ml/min]

The table above shows the results of the in vivo test in terms of air which could be detected via the air bubble counter (ABC) after a given time after the injection.

Further air injection tests were done in this setup, i.e. injection of air before and after the dialyzer (S3 and S4), which air was then removed by the degassing device on the venous side. These results were compared to the degassing efficiency in cases where the air injection was done at S1 and S2 and removed from the system by the degassing device on the arterial side of the system.

As various changes could be made in the above constructions without departing from the scope of the present disclosure, it is intended that all matter contained in the above description or shown in the accompanying drawings shall be interpreted as illustrative and not limiting.

The invention claimed is:

1. A degassing device for degassing gas bubbles out of a liquid, the degassing device comprising a housing defining a single chamber, the housing having a liquid inlet, a liquid outlet and a gas bubble outlet, the housing further comprising a spiral wall defining a spiral flow path for the liquid and a hydrophobic membrane coated with a defoaming agent and placed above the spiral wall and between the spiral wall and the gas bubble outlet without touching the spiral wall; wherein the spiral wall consists of vertical walls with an open top end; the spiral wall forcing liquid entering the housing tangentially through the liquid inlet into a spiral flow along the spiral flow path, and causing an upward flow of the gas bubbles towards the hydrophobic membrane without gas bubbles sticking to the membrane.

2. The degassing device according to claim 1, wherein a spacing is provided between the spiral wall and the hydrophobic membrane in order to maximize the contact area between the liquid and the hydrophobic membrane.

3. The degassing device according to claim 1 wherein the housing comprises a hole located on a bottom side of the housing through which hole the liquid can leave the housing.

4. The degassing device according to claim 1 wherein the housing comprises a cylindrical housing.

5. The degassing device according to claim 4 wherein the diameter of the cylindrical housing is larger than its height.

6. The degassing device according to claim 5 wherein the ratio between the diameter and the height of the cylindrical housing is in the range between 2.5:1 and 1:1.

7. The degassing device according to claim 6 wherein the ratio between the diameter and the height of the cylindrical housing is in the range between 2:1 and 1.75:1.

8. The degassing device according to claim 7 wherein the ratio between the diameter and the height of the cylindrical housing is in the range between 1.9:1 and 1.8:1.

9. The degassing device according to claim 1 wherein the liquid outlet comprises a nipple which defines an outlet passage.

10. The degassing device according to claim 9 wherein the nipple is molded integrally with the housing.

11. The degassing device according to claim 1 wherein the liquid outlet is configured to receive a first end of a tube.

12. The degassing device according to claim 11 wherein the tube forms an integral part of the liquid outlet, the tube further comprising at a second end opposite to the first end an integrated male luer.

13. The degassing device according to claim 1 wherein the liquid inlet comprises a nipple which defines an inlet passage.

14. The degassing device according to claim 13 wherein the nipple is molded integrally with the housing and is configured to receive a first end of a tube.

15. The degassing device according to claim 14 wherein the tube forms an integral part of the liquid inlet, the tube further comprising at a second end opposite to the first end an integrated male luer.

16. The degassing device according to claim 1 wherein the housing is formed from a material chosen from the group of materials consisting of polyurethane, polycarbonate, polystyrene, polymethyl methacrylate, and polypropylene.

17. The degassing device according to claim 1 and further comprising a protective member for protecting the hydrophobic membrane against external force and for limiting deformation of the hydrophobic membrane when the pressure of the liquid within the degassing device exceeds a limit.

18. The degassing device according to claim 1 wherein the hydrophobic membrane is made from a material chosen from the group of materials consisting of polyurethane, polypropylene, polyethylene, polymethylpentene, and polytetrafluoroethylene.

19. A dialysis setup, the setup comprising a pressure sensor, a first air bubble counter, a pump, a first degassing device according to claim 1, and a dialyzer.

20. The dialysis setup according to claim 19, the first degassing device being positioned on an arterial side of the setup, thus effectively removing any gas which may be present in the setup before such gas enters the dialyzer.

21. A dialysis setup comprising a first pressure sensor, a first air bubble counter, a pump, a first degassing device according to claim 1, a second degassing device according to claim 1, a second pressure sensor, a second air bubble counter, and a dialyzer.

22. The dialysis setup according claim 21, the second degassing device being positioned on a venous side of the setup, after the dialyzer.

* * * * *

UNITED STATES PATENT AND TRADEMARK OFFICE
CERTIFICATE OF CORRECTION

PATENT NO.       : 8,444,586 B2
APPLICATION NO. : 12/937901
DATED            : May 21, 2013
INVENTOR(S)      : Christof Beck It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 340 days.

Signed and Sealed this
Eighth Day of September, 2015

Michelle K. Lee
*Director of the United States Patent and Trademark Office*